(12) United States Patent
Prevot (10) Patent No.: US 12,035,765 B2
(45) Date of Patent: Jul. 16, 2024

(54) PROTECTIVE FACE SHIELD ASSEMBLY

(71) Applicant: Honeywell International Inc., Morris Plains, NJ (US)

(72) Inventor: Tanguy Prevot, Brno-Venkov (CZ)

(73) Assignee: Honeywell International Inc., Morris Plains, NJ (US)

( * ) Notice: Subject to any disclaimer, the term of this patent is extended or adjusted under 35 U.S.C. 154(b) by 733 days.

(21) Appl. No.: 16/423,903

(22) Filed: May 28, 2019

(65) Prior Publication Data

US 2020/0375281 A1 Dec. 3, 2020

(51) Int. Cl.
*A41D 13/11* (2006.01)
*A61F 9/02* (2006.01)
*A62B 23/02* (2006.01)
*D04B 1/24* (2006.01)

(52) U.S. Cl.
CPC ...... *A41D 13/1161* (2013.01); *A41D 13/1184* (2013.01); *A61F 9/025* (2013.01); *A61F 9/029* (2013.01); *A62B 23/02* (2013.01); *A41D 13/11* (2013.01); *A41D 13/1146* (2013.01); *A61F 9/027* (2013.01); *D04B 1/24* (2013.01); *D10B 2501/042* (2013.01)

(58) Field of Classification Search
CPC ................ A41D 13/11; A41D 13/1161; A41D 13/1184; A41D 13/1146; A61F 9/029; A61F 9/027; A61F 9/025; A62B 23/02; D04B 1/24; D10B 2501/042
USPC .................................................. 2/9
See application file for complete search history.

(56) References Cited

U.S. PATENT DOCUMENTS

| | | | | | |
|---|---|---|---|---|---|
| 2,579,942 | A | * | 12/1951 | MacLean ................ | A61F 9/068 D29/107 |
| 2,631,287 | A | * | 3/1953 | Malcom, Jr. ............ | A61F 9/025 2/9 |
| 2,731,637 | A | * | 1/1956 | Harry ...................... | A61F 9/025 2/9 |
| 2,758,307 | A | * | 8/1956 | Treiber .............. | A41D 13/1184 2/9 |

(Continued)

OTHER PUBLICATIONS

3M Versaflo Faceshield Assembly with Premium Visor and Faceseal, M-107, [brochure, online], [retrieved 2019], <https://www.3mcanada.ca/3M/en_CA/company-ca/all-3m-products/~/3M-Versaflo-Faceshield-Assembly-with-Premium-Visor-and-Faceseal-M-107> 4 pages.

(Continued)

*Primary Examiner* — Khaled Annis
*Assistant Examiner* — Dakota Marin
(74) *Attorney, Agent, or Firm* — Alston & Bird LLP (57) ABSTRACT

A protective face shield assembly is provided. The example protective face shield assembly includes a protective element, a frame, and a face seal. The frame defines a continuous inner frame edge and a continuous outer frame edge. The face seal includes a top portion, a bottom portion, and two side portions as a continuous unit, defining a continuous inner face seal edge and a continuous outer face seal edge. The continuous inner face seal edge is removably affixed against the continuous inner frame edge. The continuous outer face seal edge encapsulates an elastic band that fits against at least a front half portion of the head and face of a user. The face seal contains one or more layers of filter medium suitable for removing particulate matter from the air that flows from exterior air space and into interior air space.

17 Claims, 8 Drawing Sheets

(56) References Cited

U.S. PATENT DOCUMENTS

| | | | | |
|---|---|---|---|---|
| 3,362,403 A * | 1/1968 | Fleming | A42B 3/288 | 128/201.24 |
| 3,789,428 A * | 2/1974 | Martin | A63B 71/10 | 2/9 |
| 4,549,542 A * | 10/1985 | Chien | A62B 18/045 | D24/110.2 |
| 4,986,282 A * | 1/1991 | Stackhouse | A61F 9/02 | 128/857 |
| 5,054,479 A * | 10/1991 | Yelland | A42B 3/286 | 2/9 |
| 5,104,430 A * | 4/1992 | Her-Mou | A62B 18/006 | 128/206.17 |
| 5,577,495 A * | 11/1996 | Murphy | A42B 3/225 | 128/201.24 |
| 6,014,971 A * | 1/2000 | Danisch | A62B 18/045 | 128/201.24 |
| 6,752,146 B1 * | 6/2004 | Altshuler | A62B 18/006 | 2/209.12 |
| 6,872,311 B2 * | 3/2005 | Koslow | B01D 37/02 | 210/507 |
| 7,007,306 B2 * | 3/2006 | Howard | A42B 3/14 | 2/9 |
| 7,210,477 B2 * | 5/2007 | Templeton | A62B 18/025 | 128/201.25 |
| 7,752,682 B2 * | 7/2010 | Van | A41D 13/11 | 2/410 |
| 8,302,599 B2 * | 11/2012 | Green | A62B 17/04 | 128/201.25 |
| 8,336,123 B2 * | 12/2012 | Gleason | A42B 3/225 | 2/9 |
| 8,534,279 B2 * | 9/2013 | Brace | A62B 18/045 | 2/5 |
| 8,850,624 B2 * | 10/2014 | Gleason | A42B 3/085 | 2/181 |
| 9,155,923 B2 * | 10/2015 | Proctor | A62B 18/02 | |
| 9,839,798 B2 * | 12/2017 | Franke | A62B 18/082 | |
| 10,016,008 B2 * | 7/2018 | Sommers | A42B 3/085 | |
| 10,016,251 B2 * | 7/2018 | Holman | A61F 9/04 | |
| 10,052,233 B2 * | 8/2018 | Yang | A61F 9/045 | |
| 10,384,084 B2 * | 8/2019 | Isham | F21L 4/00 | |
| 10,441,019 B2 * | 10/2019 | Huh | A42B 3/14 | |
| 10,470,505 B2 * | 11/2019 | Chua | A42B 3/105 | |
| 10,667,568 B2 * | 6/2020 | Rosati | A41D 1/002 | |
| 10,709,911 B2 * | 7/2020 | Pavalarajan | A42B 3/286 | |
| 10,959,493 B2 * | 3/2021 | Raynolds | A42B 3/288 | |
| 11,033,060 B1 * | 6/2021 | Yelken | A62B 18/08 | |
| 11,273,333 B2 * | 3/2022 | Sabolis | A41D 13/1153 | |
| 2005/0066427 A1 * | 3/2005 | Gafforio | A42B 3/24 | 2/422 |
| 2005/0190549 A1 * | 9/2005 | Donaldson | A42B 3/225 | 362/105 |
| 2007/0050898 A1 * | 3/2007 | Larson | A62B 18/045 | 2/456 |
| 2011/0094020 A1 * | 4/2011 | Brookman | A62B 17/006 | 2/457 |
| 2014/0190492 A1 * | 7/2014 | Noh | A41D 13/1161 | 128/863 |
| 2018/0177251 A1 * | 6/2018 | Yoo | A41D 13/1161 | |
| 2018/0338550 A1 * | 11/2018 | Boulware | A41D 13/1161 | |

OTHER PUBLICATIONS

E-breath Face Shield Multimask Pro & Mulitmask, , [brochure, online], [retrieved 2019], <https://e-breathesafety.com>, 6 pages.

* cited by examiner

PROTECTIVE FACE SHIELD ASSEMBLY

TECHNOLOGICAL FIELD

This disclosure generally relates to a face shield assembly and, more particularly, to the configurations of a protective face shield assembly with attached filter media for respiratory protection.

BACKGROUND

Certain types of working environments, such as the ones that involve wood work, sanding, wood turning, metal sanding and grinding, stone cutting, painting, demolition, and the like, may involve various occupational hazards due to which the workers must use various types of protective gear. Such protective gear provides basic level to high-level protection to the workers from both the coarse particles and fine particulate particles as well in such types of working environments. Applicant has identified several deficiencies and problems associated with conventional grounding devices. Through applied effort, ingenuity, and innovation, many of these identified problems have been solved by developing solutions that are included in embodiments of the present invention, many examples of which are described in detail herein.

This Background section is intended to introduce the reader to various aspects of the present disclosure, which are described and/or claimed below. This discussion is believed to help provide the reader with background information to facilitate a better understanding of the various aspects of the present disclosure. Accordingly, it should be understood that these statements are to be read in this light.

BRIEF SUMMARY

Conventional face shields and/or protective eye-wear may be used by workers to avoid contact with coarse particles, such as dust or curls projections, as the impact of such particles is instantaneous. However, such eye-wear and/or face shields typically leave gaps between the edge of the eye-wear and/or face shields and the neck or forehead.

Further, there are also associated respiratory risks in such working environments. Most of the workers have lower safety awareness about the respiratory risks, as such respiratory risks are less evident at present, but may potentially harm workers in the long run. Some workers do wear disposable masks for a basic level of protection, i.e., TH1, along with the eye-wear and/or face shields. However, such disposable masks require a correct fit for best protection and aren't generally comfortable to wear because of the direct skin contact on the face, and especially the sensitive areas around the mouth and nose.

There are also available other face shields, such as PAPR face shields, that may achieve a higher level of protection, i.e., TH2 or TH3. However, such PAPR face shields are very costly and only appeal to workers who are very aware of serious respiratory risks. The PAPR face shields may be too advanced for workers who only need TH1 level of respiratory protection or the workers who are occasionally exposed to respiratory risks. Further, such PAPR face shields may feature a textile or foam face seal, all along the edge of the protective face shield, around the chin and cheeks. However, such face seal acts as a barrier and offers very high breathing resistance.

A protective face shield assembly described herein addresses these deficiencies and others by addition of a face seal to the protective face shield, the face seal acting as a non-powered filter medium. The proposed face shield assembly described herein thus provides light, comfortable, and affordable basic-level respiratory protection to current users of face shields (particularly the ones involved in work environments involving wood work, sanding, wood turning, metal sanding and grinding, stone cutting, and the like). The proposed face shield assembly described herein reduces breathing resistance and improves the basic level of respiratory protection for the user.

With reference to the claimed face shield assembly, the protective face shield may comprise a protective element including an outer edge. The protective face shield may further include a frame including a front band structure, a bottom band structure, and side band structures. The front band structure, the bottom band structure, and the side band structures of the frame may define a continuous inner frame edge and a continuous outer frame edge. The continuous outer frame edge may define an opening sized to fit the outer edge of the protective element. The protective face shield may further include a face seal including a top portion, a bottom portion, and side portions as a continuous unit. The top portion, the bottom portion and the side portions of the face seal may define a continuous inner face seal edge and a continuous outer face seal edge. The continuous inner face seal edge may be removably affixed against the continuous inner frame edge of the frame. The continuous outer face seal edge may encapsulate an elastic band that may fit against at least a front half of a head and face portion of a user. The face seal may contain one or more layers of filter medium suitable for removing particulate matter from the air that flows from an exterior air space and into an interior air space.

The protective face shield may further include a head suspension member adapted to support the frame through an adjustable top support member and an adjustable back support member. The adjustable top support member may be configured to provide a top support to the frame. The adjustable back support member may be configured to provide a back support to the frame.

In some embodiments, the adjustable back support member may comprise an additional support member adapted to provide additional support to the frame from the back portion of the head. In some embodiments, fitting of the adjustable back support member may be controlled by a knob member positioned at the adjustable back support member.

In some embodiments, the continuous outer frame edge of the frame may have a groove structure that may receive the outer edge of the protective element and lock the protective element in the groove structure using a snap and fit mechanism.

An interface between the outer edge of the protective element and the continuous outer frame edge of the frame may be air-tight to create an air path of maximum resistance for air flow. Further, another interface between the continuous inner frame edge of the frame and the continuous outer face seal edge of the face seal may be air-tight to create an air path of maximum resistance for air flow.

In some embodiments, the one or more layers of filter medium of the face seal may create an air path of least resistance for air flow.

The exterior air space may correspond to an air space outside the protective face shield, and the interior air space may correspond to air space inside the protective face shield.

In some embodiments, the continuous inner face seal edge may be affixed against the continuous inner frame edge of the frame to prevent air leakage using double-sided adhesive tape. In alternate embodiments, the continuous inner face seal edge may be affixed against the continuous inner frame edge of the frame to prevent air leakage using a hook and loop fastener. In alternate embodiments, the continuous inner face seal edge may be affixed against the continuous inner frame edge of the frame to prevent air leakage using a push-and-fit mechanism.

In some embodiments, one of the frame or the face seal may include an active ventilator configured to regulate air flow from the interior air space to the exterior air space.

In some embodiments, the face seal containing the one or more layers of the filter medium may have pleats to increase an effective surface area of the face seal.

In some embodiments, at least one of the one or more layers of the filter medium comprises filter membranes made from nanofibers.

In some embodiments, the inner surface of the protective element may be a hydrophilic surface.

In another aspect of the disclosure, a protective face shield assembly is disclosed that comprises a protective element including an outer edge. The protective face shield assembly may further comprise a frame including a semi-circular front band structure affixed with a head support member and having end portions, a curved bottom band structure, and side band structures opposite and parallel to each other with chamfered lower end portions. The side band structures may connect the opposite end portions, respectively, of the semi-circular front band structure with the curved bottom band structure to form a unified structure of the frame. The semi-circular front band structure, the curved bottom band structure, and the side band structures of the frame may define a continuous inner frame edge and a continuous outer frame edge. The continuous outer frame edge may define an opening sized to fit the outer edge of the protective element using a snap and fit mechanism. The protective face shield assembly may further comprise a face seal including a top portion, a bottom portion, and side portions as a continuous unit, wherein the top portion, the bottom portion and the side portions of the face seal define a continuous inner face seal edge and a continuous outer face seal edge. The continuous inner face seal edge may be affixed against the continuous inner frame edge of the frame to prevent air leakage using a hook and loop mechanism. The continuous outer face seal edge may encapsulate an elastic band that fits against at least a front half of a head and face portion of a user. The face seal may contain one or more layers of filter medium suitable for removing particulate matter from the air that flows from an exterior air space and into an interior air space. The protective face shield assembly may further comprise a head suspension member adapted to support the frame through an adjustable top support member and an adjustable back support member.

The adjustable top support member may be designed to be substantially in an orthogonal plane with respect to the semi-circular front band structure. Two ends of the adjustable top support member may be engaged with opposite ends of the semi-circular front band structure to provide a top support to the frame. The adjustable back support member orthogonally may extend out from the adjustable top support member and chamfer downward towards a back portion of the frame. The adjustable back support member may comprise an additional support member adapted to provide additional support to the frame from a back portion of the head. Fitting of the adjustable back support member may be controlled by a knob member positioned at the adjustable back support member.

In some embodiments, the continuous outer frame edge of the frame may have a groove structure that receives the outer edge of the protective element and locks the protective element in the groove structure using the snap and fit mechanism.

In some embodiments, the protective element may be permanently fixed in the continuous outer frame edge of the frame. In some alternate embodiments, the protective element may be a part of the unified structure of the frame.

In some embodiments, an interface between the outer edge of the protective element and the continuous outer frame edge of the frame may be air-tight to create an air path of maximum resistance for air flow. Another interface between the continuous inner frame edge of the frame and the continuous outer face seal edge of the face seal may be air-tight to create an air path of maximum resistance for air flow.

In some embodiments, the one or more layers of the filter medium of the face seal may create an air path of least resistance for air flow. In some embodiments, the exterior air space may correspond to an air space outside the protective face shield assembly, and the interior air space may correspond to an air space inside the protective face shield assembly.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in some embodiments described herein. Some embodiments may include fewer (or more) components than those shown in the figures.

Like reference symbols in the various drawings indicate like elements.

DETAILED DESCRIPTION

With reference to FIGS. 1A to 1E, a protective face shield assembly 100, as a general and respiratory protection gear, is illustrated comprising an example frame 102 and an example face seal 104. While described herein with reference to a specific structure of the protective face shield assembly 100, the present disclosure contemplates that the embodiments described herein may be equally applicable to other designs and structures of face shields. The present disclosure appreciates that a protective face shield assembly (e.g., face shield assembly 100) may refer to a particular implementation of a frame removably affixed with an example face seal. For the sake of consistency of description, however, reference herein is made to a protective face shield assembly as an example. While illustrated herein with a particular shape and configuration, the present disclosure contemplates that the protective face shield assembly 100 may be in various designs, form factors, housings, and the like based upon the intended application of the face seal 104, such as illustrated in FIGS. 2A and 2B.

Figure 1A:
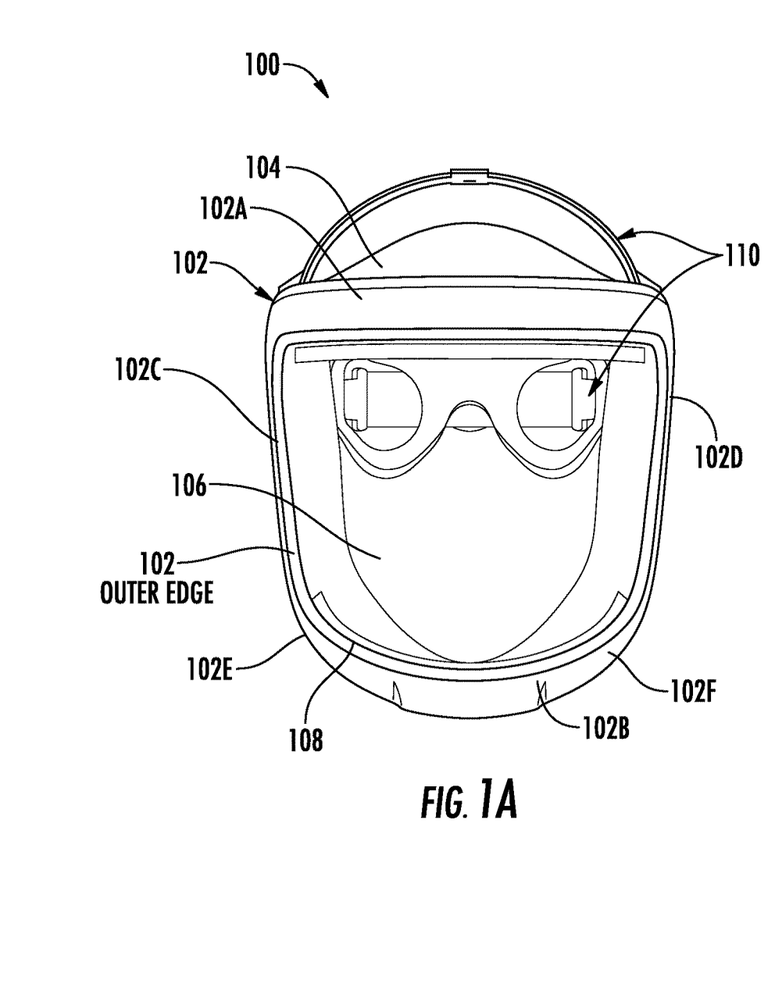
FIG. 1A is a front view of a face shield assembly in accordance with an example embodiment of the present disclosure.
Figure 1B:
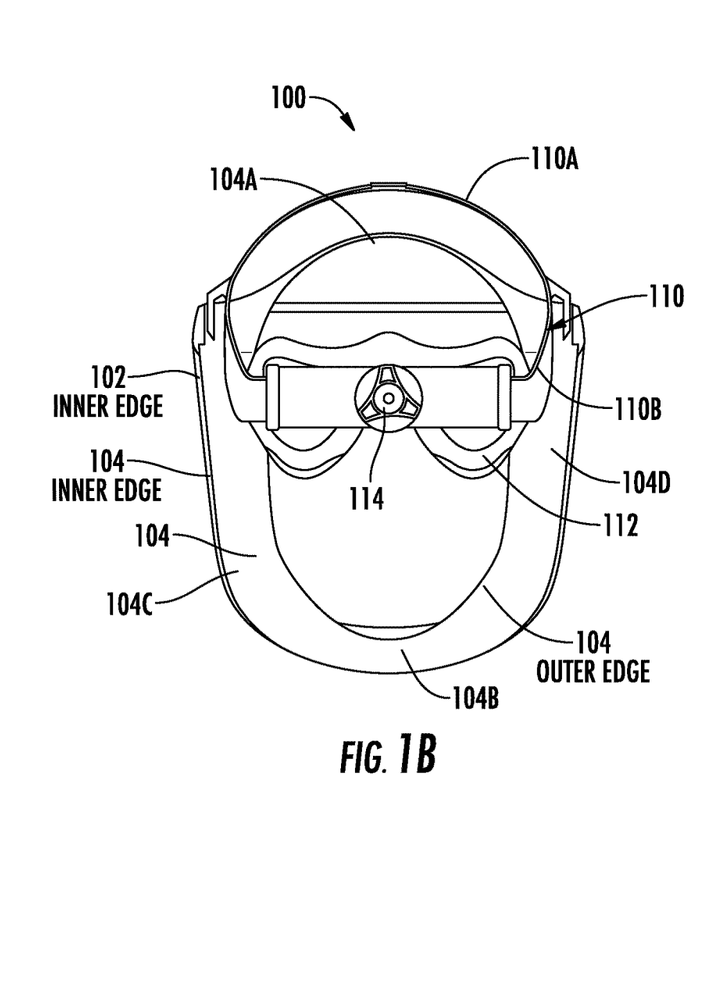
FIG. 1B is a rear view of the face shield assembly shown in FIG. 1A.
Figure 1C:
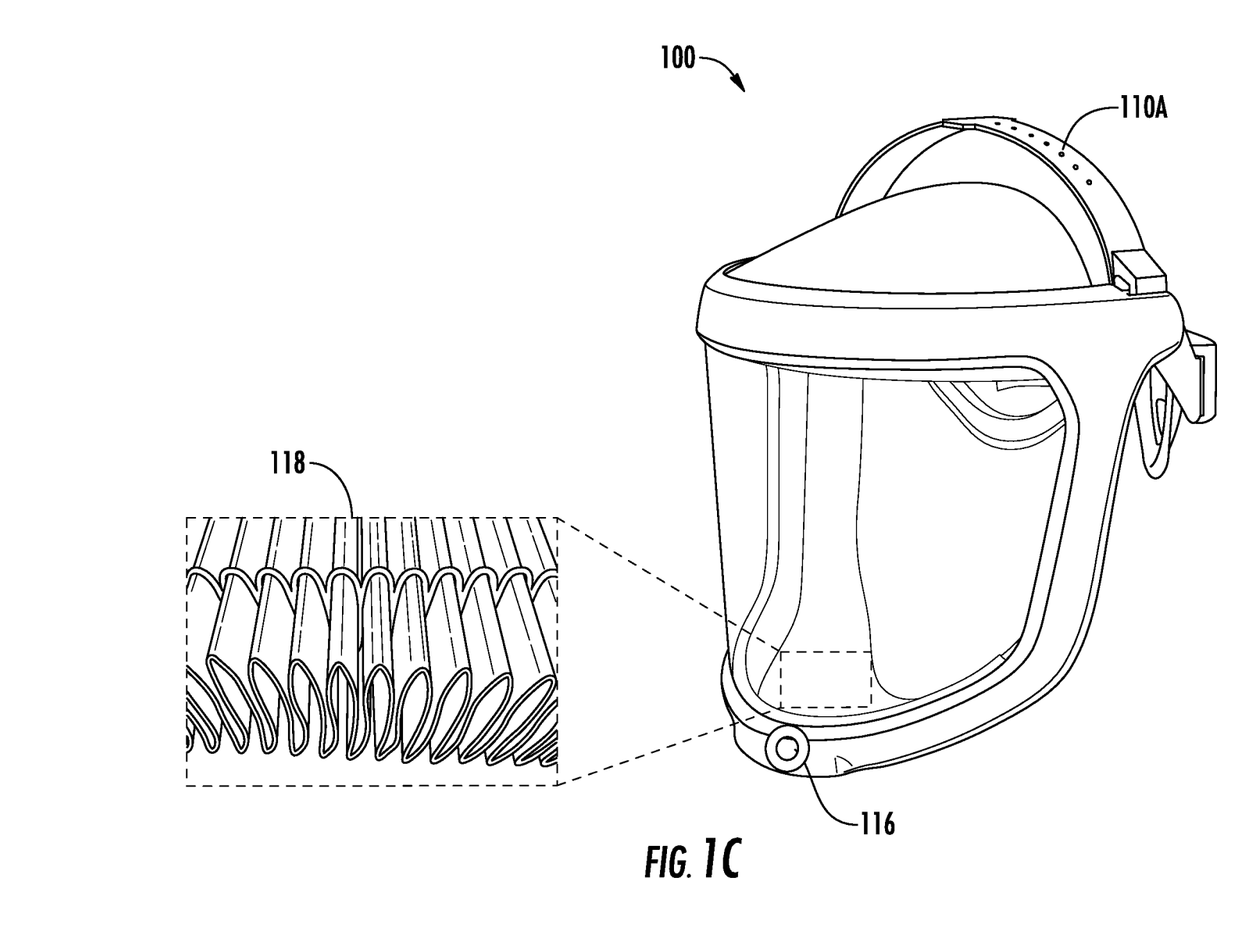
FIG. 1C is a perspective view of the face shield assembly shown in FIGS. 1A & 1B.
Figure 1D:
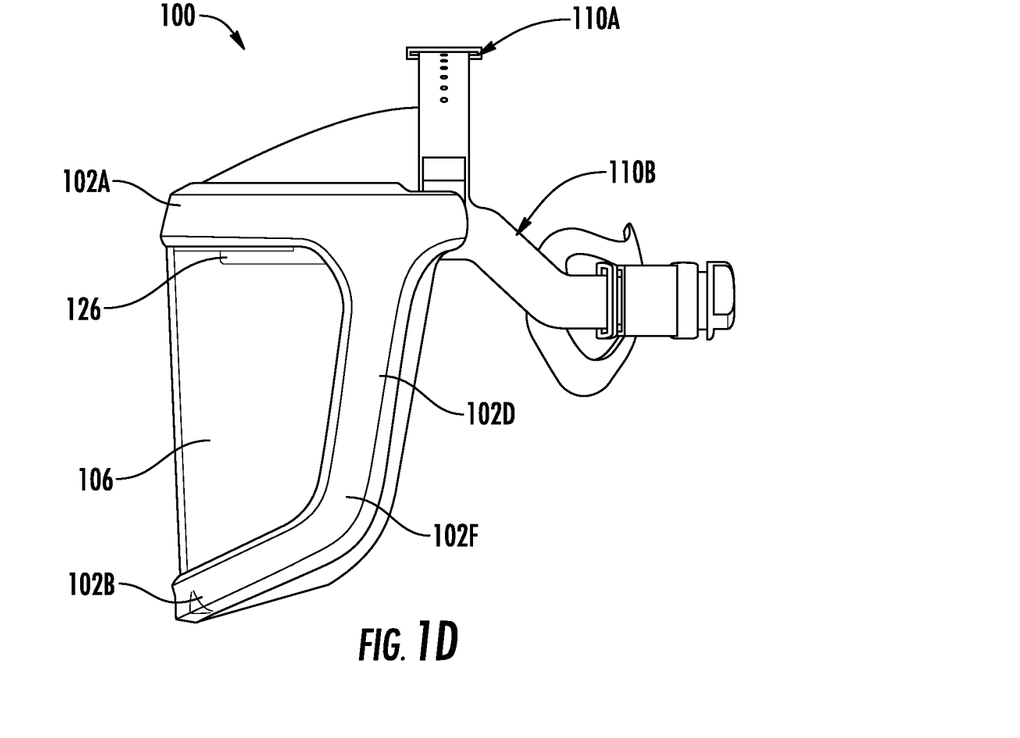
FIG. 1D is a left side view of the face shield assembly shown in FIGS. 1A-1C.
Figure 1E:
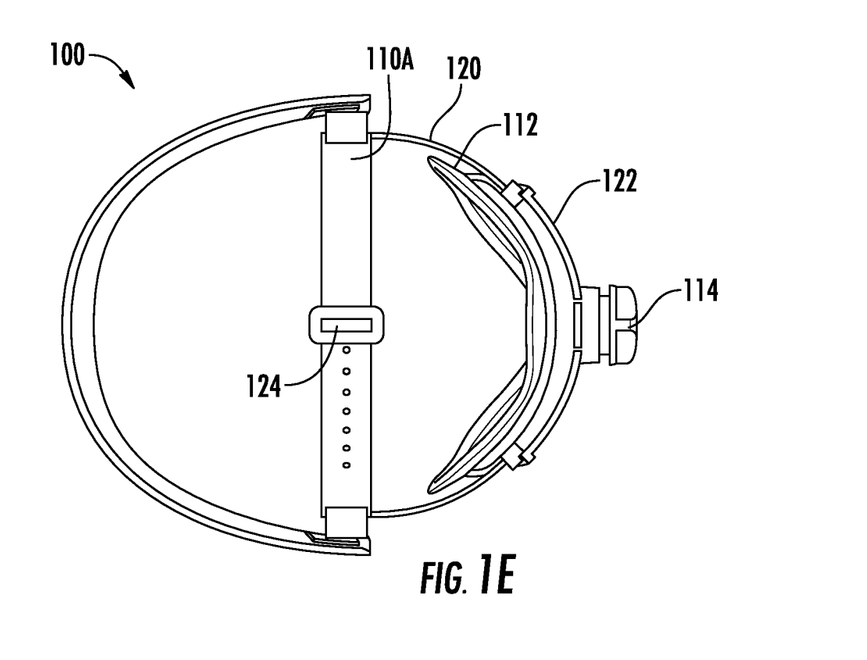
FIG. 1E is a top view of the face shield assembly shown in FIGS. 1A-1D.
Figure 2A:
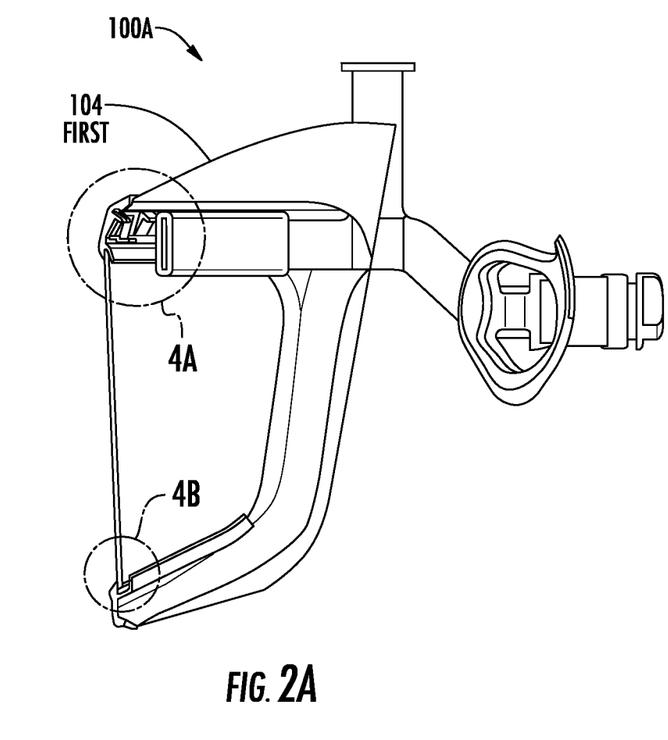
FIG. 2A is a cross-sectional view of the face shield assembly shown in FIG. 1A having a face seal in accordance with one embodiment.
Figure 2B:
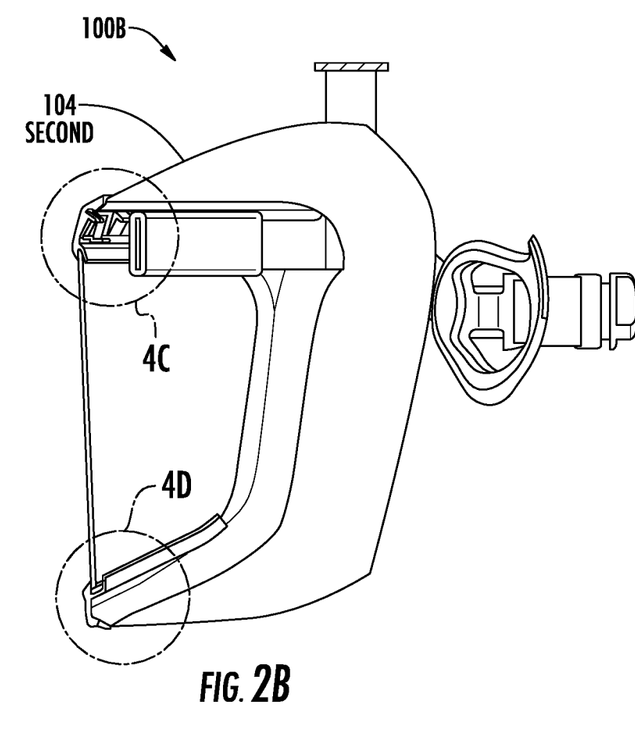
FIG. 2B is a cross-sectional view of a face shield similar to the face shield assembly shown in FIG. 1A having a face seal in accordance with another embodiment.

FIGS. 1A to 1E illustrate various views of the protective face shield assembly 100, according to an example embodiment. Particularly, FIG. 1A illustrates a front view, FIG. 1B illustrates a rear view, FIG. 1C illustrates a perspective view, FIG. 1D illustrates a left side view, and FIG. 1E illustrates a top view of the protective face shield assembly 100.

With reference to FIGS. 1A to 1E, there is illustrated the protective face shield assembly 100 for respiratory, ocular, and facial protection. The protective face shield assembly 100 includes the frame 102, the face seal 104, and a protective element 106. The protective element 106 may be removably fitted in an opening 108 of the frame 102. The protective face shield assembly 100 may also include a head suspension member 110 in order to provide suitable support when the protective face shield assembly 100 is worn by a user. The head suspension member 110 may be altered to accommodate various head sizes of different users, thereby enabling the protective face shield assembly 100 for being used as a free-size or universal size face shield assembly. The head suspension member 110 may include an adjustable top support member 110A, an adjustable back support member 110B, an additional support member 112, and a knob member 114. There is further shown an active ventilator 116 and a pleated filter medium 118, in accordance with various embodiments. The adjustable back support member 110B further includes a slidable member 120 and a bracket member 122. The adjustable top support member 110A may include a buckle member 124.

The frame 102 preferably includes a semi-circular front band structure 102A (hereinafter front band structure 102A), a curved bottom band structure 102B (hereinafter bottom band structure 102B), and side band structures 102C and 102D. In use, the front band structure 102A may be affixed with a forehead support member 126. The forehead support member 126 having a foamed layer may abut the forehead when the protective face shield assembly 100 is worn by the user. The front band structure 102A, the bottom band structure 102B, and the side band structures 102C and 102D are preferably fabricated as a single, unitary member out of lightweight material, for example, polycarbonate or nylon although other lightweight materials may be utilized, as would be known to those of skill in the art. The side band structure 102C connects one end portion of the front band structure 102A, and extends through a chamfered lower end portion 102E to the one end portion of the bottom band structure 102B. Similarly, the side band structure 102D connects other end portion of the front band structure 102A and extends through other chamfered lower end portion 102F to the other end portion of the bottom band structure 102B. Accordingly, the frame 102 may be formed as a unified structure.

The unified structure of the frame 102 thus defines a continuous inner frame edge $102_{Inner\ Edge}$ and a continuous outer frame edge $102_{Outer\ Edge}$. The unified structure of the frame 102 further defines an opening 108 that is bounded by the continuous outer frame edge $102_{Outer\ Edge}$. The opening 108 may be sized to receive the protective element 106 and preferably extends from a centerline of the protective face shield assembly 100 toward the side band structures 102C and 102D of the protective face shield assembly 100, so that the frame 102 does not obstruct the peripheral vision of the user. The protective element 106 may be received in the opening 108 by various mechanisms, such as a snap and fit mechanism, as described in FIGS. 4A and 4B.

Once the protective element 106 is received in the opening 108, the interface between the outer edge of the protective element 106 and the continuous outer frame edge $102_{Outer\ Edge}$ of the frame 102 must become air-tight to create an air path of maximum resistance for air flow. The interface between the outer edge of the protective element 106 and the continuous outer frame edge $102_{Outer\ Edge}$ of the frame 102 should be such that there is no chance of any air leakage through the interface.

In certain example embodiments, the protective element 106 may be permanently fixed in the continuous outer frame edge $102_{Outer\ Edge}$ of the frame 102. Thus, in such example embodiments, the protective element 106 becomes a part of the unified structure of the frame 102. In other embodiments, the protective element 106 may be supported within the frame 102 with the use of fasteners. In such cases, there may be required corresponding openings for receiving fasteners in the protective element 106.

The protective element 106 may be a lens made of a substantially transparent material or may be made of such other suitable material known in the art. The protective element 106 may be preferably formed as a single, unitary member having a shape defined by an outer peripheral edge, which is preferably continuous. The protective element 106 may be preferably injection molded into a sheet made of, for example, polycarbonate, acrylic, polyester, or any other of a variety of materials that are well known in the art. The protective element 106 may be pre-molded into a spherical or another rounded shape. The protective element 106 may be preferably shaped and sized to fit into the shape and size of the opening 108 provided in the frame 102. In certain example embodiments, the inner surface of the protective element 106 may be a hydrophilic surface. The protective element 106 may also be coated with a variety of chemical coatings, depending upon a particular application. For example, the protective element 106 may have an anti-fog coating, a reflective coating, or a coating applied to improve the chemical and/or scratch resistance of the protective element 106, or any other coating as is well known in the art.

The protective face shield assembly 100 may also include the face seal 104 that includes a top portion 104A, a bottom portion 104B, and side portions 104C and 104D as a continuous unit. The top portion 104A, the bottom portion 104B, and the side portions 104C and 104D of the face seal 104 collectively define a continuous inner face seal edge $104_{Inner\ Edge}$ and a continuous outer face seal edge $104_{Outer\ Edge}$. In some embodiments, the continuous inner face seal edge $104_{Inner\ Edge}$ may be removably affixed against the continuous inner frame edge $102_{Inner\ Edge}$ of the frame 102 to prevent air leakage. In some alternative embodiments, the continuous inner face seal edge $104_{Inner\ Edge}$ may be affixed against the continuous inner frame edge $102_{Inner\ Edge}$ of the frame 102 to prevent air leakage. The continuous inner face seal edge $104_{Inner\ Edge}$ may be affixed against the continuous inner frame edge $102_{Inner\ Edge}$ of the frame 102 by various mechanisms, as illustrated in FIGS. 3A to 3C and 4C and 4D.

The continuous outer face seal edge $104_{Outer\ Edge}$ encapsulates an elastic band that perfectly fits against at least a front half of a head and face portion of the user, as illustrated in FIG. 2A or the complete head and face portion of the user, as illustrated in FIG. 2B. Such elastic band encapsulated at the continuous outer face seal edge $104_{Outer\ Edge}$ may facilitate a proper fitting against the head and/or face of the user and at the same time prevent any air leakage. Further, such elastic band encapsulated at the continuous outer face seal edge $104_{Outer\ Edge}$ may maintain the proper fitting against the head and/or face of the user even when the user moves the head around while working.

The face seal 104 may contain one or more layers of filter medium suitable for removing particulate matter from the air that flows from an exterior air space and into an interior air space of the protective face shield assembly 100. The exterior air space corresponds to an air space outside the protective face shield assembly 100, and the interior air space corresponds to air space inside the protective face shield assembly 100.

In an example embodiment, at least one of the one or more layers of the filter medium may be formed by electrospinning a material as nanofibers. In some embodiments, the nanofibers are formed by electrospinning a polymer solution that may be further functionalized by the addition of another material to the polymer solution. The additional functionalizing material may be operable to remove gases and may comprise one or more chemicals that may capture gases (where the gases might be volatile organic chemicals (VOCs), acid vapors, carbon dioxide ($CO_2$), nitrogen monoxide (NO), nitrogen dioxide (N(¾)), ozone ($O_3$), hydrogen cyanide (HCN), arsine ($AsH_3$), hydrogen fluoride (HF), chlorine dioxide ($ClO_2$), ethylene oxide ($C_2H_4O$), formaldehyde ($CH_2O$), methyl bromide ($CH_3Br$), and/or phosphine ($PH_3$)). In an embodiment, the functionalized material may comprise one of a biocide (i.e. a chemical substance or microorganism which can deter, render harmless, or exert a controlling effect on any harmful organism by chemical or biological means), a virucide (i.e. a physical or chemical agent that deactivates or destroys viruses) and/or a bactericide (i.e. a substance that kills bacteria, for example disinfectants, antiseptics, or antibiotics). In other embodiments, the functionalized nanofiber may be operable to remove humidity, control temperature, indicate the end of service life, indicate clogged material, and/or provide a fresh odor inside the face seal 104. Other layers of the one or more layers of the filter medium may be utilized to increase the filtering level of the face seal 104, however at the same time, the one or more layers of the filter medium must provide a suitable breathing resistance when the protective face shield assembly 100 is worn by the user.

In some embodiments, as illustrated in FIG. 1C, the frame 102 of the protective face shield assembly 100 may accommodate an active ventilator 116 configured to facilitate the mitigation of, for example, the risk of fogging on the protective element 106 due to moisture from the breath of the user. The active ventilator 116 may be further configured to expel hot, humid, carbon dioxide-enriched exhaust air, and heat pile-up from inside the protective face shield assembly 100 during prolonged usage by the user. In such embodiments, the active ventilator 116 may be battery-powered and rechargeable by use of micro-USBs, for example.

In some embodiments, as illustrated in FIG. 1C, the face seal 104 of the protective face shield assembly 100 may be in the form of the pleated filter medium 118. Such pleated filter medium 118 may effectively increase the surface area of the face seal 104 of the protective face shield assembly 100. Accordingly, the shelf-life of the face seal 104 of the protective face shield assembly 100 may almost double in such embodiments.

As illustrated clearly in FIGS. 1D and 1E, the protective face shield assembly 100 may also include the head suspension member 110 in order to provide suitable support when the protective face shield assembly 100 is worn by the user. The head suspension member 110 may be adapted to support the frame 102 through the adjustable top support member 110A and the adjustable back support member 110B. The adjustable top support member 110A may be designed to be substantially in an orthogonal plane with respect to the front band structure 102A. The two ends of the adjustable top support member 110A may be engaged with opposite ends of the front band structure 102A to provide top support to the frame 102. As illustrated in FIG. 1E, the adjustable top support member 110A may be provided with the buckle member 124, using which the adjustable top support member 110A may be adjusted according to the required fitting or suspension level based on the face and/or head size of the user.

Further, the adjustable back support member 110B may orthogonally extend out from the adjustable top support member 110A and chamfer downward towards the back portion of the frame 102. The adjustable back support member 110B may comprise the additional support member 112 adapted to provide additional support to the frame 102 from the back portion of the head of the user. The circumferential fitting of the additional support member 112 may be controlled by a knob member 114 positioned at the adjustable back support member 110B. The fitting mechanism is described in further detail in FIGS. 5A and 5B.

FIGS. 2A and 2B illustrate face seals having different designs and form factors, according to example embodiments. Particularly, FIG. 2A illustrates a first design of a face seal $104_{First}$ of an example protective face shield assembly 100A, and FIG. 2B illustrates a second design of another face seal $104_{Second}$ of another example face shield assembly 100B.

While illustrated herein with different shapes and configurations, the present disclosure contemplates that the example face shield assemblies 100A and 100B in two different designs, form factors, housings, and the like are based upon the intended application of corresponding face seals, such as illustrated in FIGS. 2A and 2B. For example, the intended application of the first design of the face seal $104_{First}$ of the example face shield assembly 100A may be in a working environment where merely face and respiratory protection is required. Thus, the first design of the face seal $104_{First}$ is such that the complete face and half portion of the head of the user is shielded by the filter medium of the face seal $104_{First}$. In such an embodiment, the continuous outer face seal edge $104_{Outer\ Edge}$ may be fitted around only the front portion of the face and head of the user.

On the contrary, the intended application of the second design of the face seal $104_{Second}$ of the other example face shield assembly 100B may be in a working environment where facial, head, and respiratory protection is required. Thus, the second design of the face seal $104_{Second}$ is such that the complete face and head of the user is shielded by the filter medium of the face seal $104_{Second}$. In such an embodiment, the continuous outer face seal edge $104_{Outer\ Edge}$ may be fitted around the neck and the nape portion of the user. While illustrated herein with two designs of the face seal, the present disclosure contemplates that the face seal may be further designed in various other designs, form factors, housings, and the like based upon the intended application of the corresponding face shield assembly.

Figure 3A:
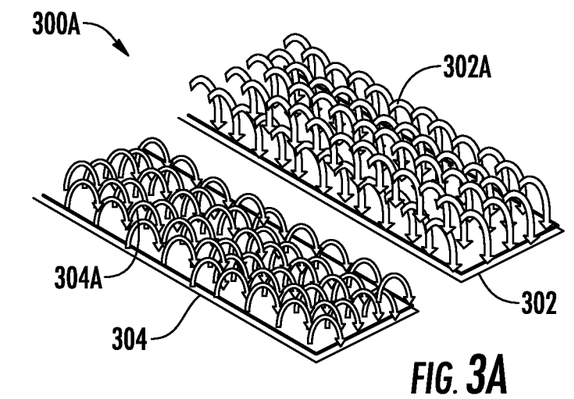
FIG. 3A shows a hook and loop material for use as an affixing mechanism by which an example continuous inner face seal edge of an example face seal may be removably affixed against an example continuous inner frame edge of an example frame, according to different example embodiments.
Figure 3B:
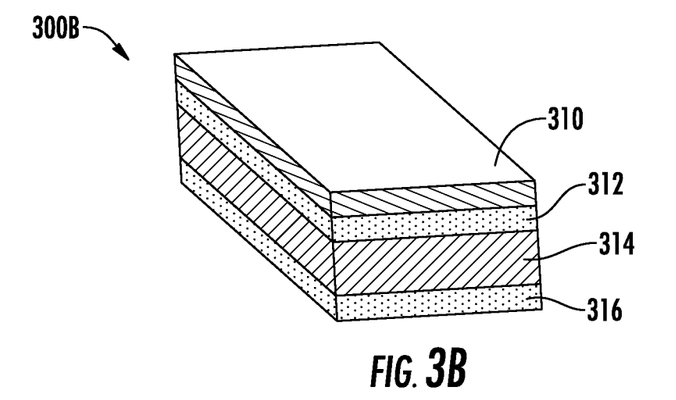
FIG. 3B shows a hook and loop material for use as an affixing mechanism by which an example continuous inner face seal edge of an example face seal may be removably affixed against an example continuous inner frame edge of an example frame, according to different example embodiments.
Figure 3C:
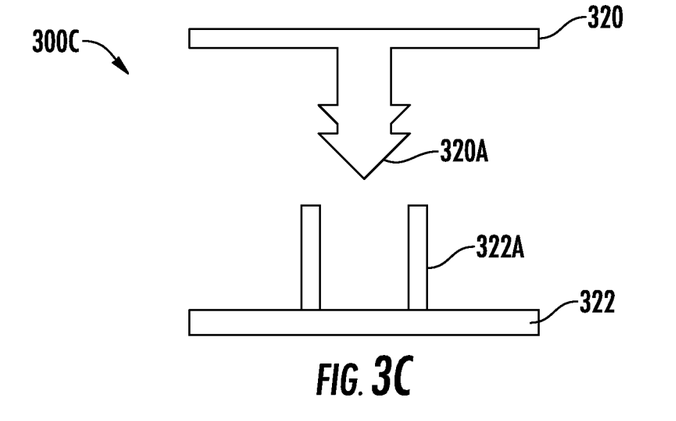
FIG. 3C shows a push-and-fit mechanism for use as an affixing mechanism by which an example continuous inner face seal edge of an example face seal may be removably affixed against an example continuous inner frame edge of an example frame, according to different example embodiments.

FIGS. 3A to 3C illustrate different types of affixing mechanisms by which the continuous inner face seal edge $104_{Inner\ Edge}$ of the face seal 104 may be removably affixed against the continuous inner frame edge $102_{Inner\ Edge}$ of the frame 102, according to different example embodiments. Particularly, FIG. 3A illustrates a first affixing mechanism 300A that corresponds to a hook-and-loop fastener, FIG. 3B illustrates a second affixing mechanism 300B that corresponds to double-sided adhesive tape and FIG. 3C illustrates a third affixing mechanism 300C that corresponds to a push-and-fit mechanism.

With reference to FIG. 3A, the first affixing mechanism 300A may correspond to a hook-and-loop fastener. Using the hook-and-loop fastener, the continuous inner face seal edge $104_{Inner\ Edge}$ may be removably affixed against the continuous inner frame edge $102_{Inner\ Edge}$ of the frame 102 to prevent air leakage. The hook-and-loop fastener, as illustrated as the first affixing mechanism 300A, consist of two lineal fabric strip components 302 and 304 which are attached (i.e., sewn or otherwise adhered) to the opposing surfaces to be fastened. The first fabric strip component 302 features tiny hooks 302A, and the second fabric strip component 304 features tiny loops 304A. When the two lineal fabric strip components 302 and 304 are pressed together, the tiny hooks 302A catch in the tiny loops 304A, and the two lineal fabric strip components 302 and 304 fasten or bind temporarily. The lineal fabric strip components 302 and 304 may be separated by pulling or peeling the two surfaces apart. It may be preferred to have the harder first lineal fabric strip component 302 affixed to the continuous inner frame edge $102_{Inner\ Edge}$ of the frame 102, due to lesser flexibility, and the softer second lineal fabric strip component 304 to be affixed to the continuous inner face seal edge $104_{Inner\ Edge}$ of the face seal 104, due to higher flexibility.

With reference to FIG. 3B, the second affixing mechanism 300B may correspond to double-sided adhesive tape. Using the double-sided adhesive tape, the continuous inner face seal edge $104_{Inner\ Edge}$ may be removably affixed against the continuous inner frame edge $102_{Inner\ Edge}$ of the frame 102 to prevent air leakage. The double-sided adhesive tape, as illustrated as the second affixing mechanism 300B, may be a pressure-sensitive tape that is coated with adhesive on both sides. The double-sided adhesive tape may seamlessly stick two surfaces, such as the continuous inner face seal edge $104_{Inner\ Edge}$ of the face seal 104 and the continuous inner frame edge $102_{Inner\ Edge}$ of the frame 102, together. The double-sided adhesive tape may consist of multiple functional layers, one of which is illustrated in FIG. 3B. With reference to FIG. 3B, there is shown a release liner 310, a first pressure sensitive adhesive 312, a carrier 314, and second pressure sensitive adhesive 316. The release liner 310 may be a paper, a film, or a silicon liner that covers the adhesive system and is coated with silicon releasing agents creating a differential release. The first pressure sensitive adhesive 312 and the second pressure sensitive adhesive 316 may correspond to a synthetic composition that binds two surfaces together and resists their separation. The first pressure sensitive adhesive 312 and the second pressure sensitive adhesive 316 may have the same or different chemistries and may further have the same or different coating thicknesses. Various examples of adhesives used as the first pressure sensitive adhesive 312 and the second pressure sensitive adhesive 316 may include, but are not limited to, acrylic adhesives, epoxy resins, rubber-based adhesives, silicone adhesives and sealants, polyurethane and isocyanate adhesives, and the like. The carrier 314 may be a means of supporting and separating adhesive coatings of, for example, the first pressure sensitive adhesive 312 and the second pressure sensitive adhesive 316. The carrier 314 may provide additional strength and stability for handling during assembly of surfaces, such as the continuous inner face seal edge $104_{Inner\ Edge}$ of the face seal 104 and the continuous inner frame edge $102_{Inner\ Edge}$ of the frame 102. Examples of types of the carrier 314, may include but are not limited to, polyester, polypropylene, polyethylene, foam, paper, and tissue. It may be preferred to have the second affixing mechanism 300B affixed to the continuous inner face seal edge $104_{Inner\ Edge}$ of the face seal 104, due the face seal 104 being a consumable.

With reference to FIG. 3C, the third affixing mechanism 300C may correspond to a push-and-fit mechanism. Using the push-and-fit mechanism, the continuous inner face seal edge $104_{Inner\ Edge}$ may be removably affixed against the continuous inner frame edge $102_{Inner\ Edge}$ of the frame 102 to prevent air leakage. The push-and-fit mechanism, as illustrated as the third affixing mechanism 300C, may include two components: a rubber profile component 320 and a plastic groove component 322. The rubber profile component 320 may include harpoon-shaped features 320A, the edges of which may get squeezed inside the plastic groove component 322 when pushed against the plastic groove component 322. After that, the plastic groove component 322 holds the harpoon-shaped features 320A between one or more elements 322A of the plastic groove component 322 until the rubber profile component 320 is pulled back. Upon pulling back the rubber profile component 320, the harpoon-shaped features 320A roll-over, overcome the friction between the harpoon-shaped features 320A and the one or more elements 322A, and are released from the plastic groove component 322. It may be preferred to have the rubber profile component 320 (being flexible) affixed to the continuous inner face seal edge $104_{Inner\ Edge}$ of the face seal 104, and the plastic groove component 322 to be affixed to the continuous inner frame edge $102_{Inner\ Edge}$ of the frame 102.

Figure 4A:
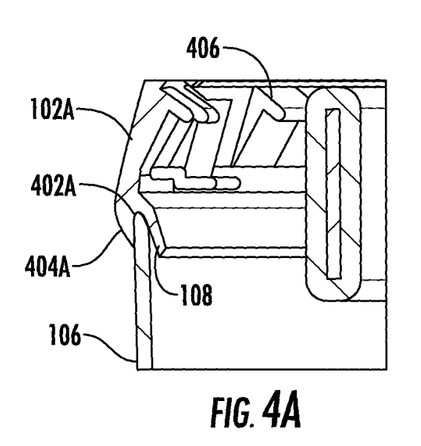
FIG. 4A shows a cross-sectional view of the face shield having a snap fit interface between an example protective element and an example opening of an example frame, according to an example embodiment.
Figure 4B:
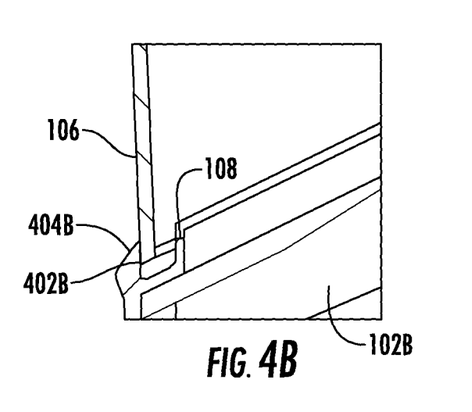
FIG. 4B shows a cross-sectional view of the face shield having a snap fit interface between an example protective element and an example opening of an example frame, according to an example embodiment.

FIGS. 4A and 4B illustrate an interfacing between the protective element 106 and the opening 108 of the frame 102, according to an example embodiment. FIGS. 4A and 4B illustrate an interfacing between the continuous inner face seal edge $104_{Inner\ Edge}$ of the face seal 104, and the continuous inner frame edge $102_{Inner\ Edge}$ of the frame 102, according to an example embodiment.

With reference to FIGS. 4A and 4B, there is illustrated an interfacing between the outer edge of the protective element 106 and the opening 108 that is bounded by the continuous outer frame edge $102_{Outer\ Edge}$ of the frame 102. The protective element 106 may be removably secured within the opening 108 of the front band structure 102A and the bottom band structure 102B by grooves or channels 402A and 402B, respectively, as illustrated in FIGS. 4A and 4B, respectively. The grooves or the channels 402A and 402B may be preferably formed between the opening 108 of the frame and lip members 404A and 404B, respectively. As best shown in FIGS. 4A and 4B, the grooves or the channels 402A and 402B formed between the opening 108 of the frame and lip members 404A and 404B, respectively, may be sized to receive the outer edges of the protective element 106. In order to more securely fit the protective element 106 into the grooves or the channels 402A and 402B, a plurality of ridges (not shown) supported on the inner surface of the lip members 404A and 404B are preferably provided. The plurality of ridges may also aid in the manufacturing process of the shell by making the lip members 404A and 404B more rigid. Any suitable number of ridges may be provided, as desired. The lip members 404A and 404B and the ridges may also be formed as a single, unitary piece with the remaining portion of the frame. Alternately, the pieces may be formed as separate members and joined in any manner, as known to those of skill in the art.

In some embodiments, the protective element 106 may include a slightly arcuate upper edge, side edges which curve slightly forward and a curved lower edge, in accordance with the shape of the opening 108 of the frame 102. The frame 102 may be sufficiently flexible so that it curves or bends without fracturing when the protective element 106 is to be fitted within the opening 108 of the frame 102 via a slide-and-fit mechanism provided by the grooves or the channels 402A and 402B and the lip members 404A and 404B. In alternative embodiments, the protective element 106 may be sufficiently flexible so that it curves or bends without fracturing when placed within the opening 108 of the frame 102 via the slide-and-fit mechanism provided by the grooves or the channels 402A and 402B and the lip members 404A and 404B. There is further shown hook fasteners 406 in FIG. 4A through which the outer and inner members of the frame 102 are snapped together via a snap-and-fit fastening mechanism. It may be noted that for brevity, only the side views of the front band structure 102A and the bottom band structure 102B are illustrated and described herein. However, the present disclosure may be contemplated to have the same interfacing all along the opening 108 of the frame 102, without any deviation from the scope of the disclosure.

Figure 4C:
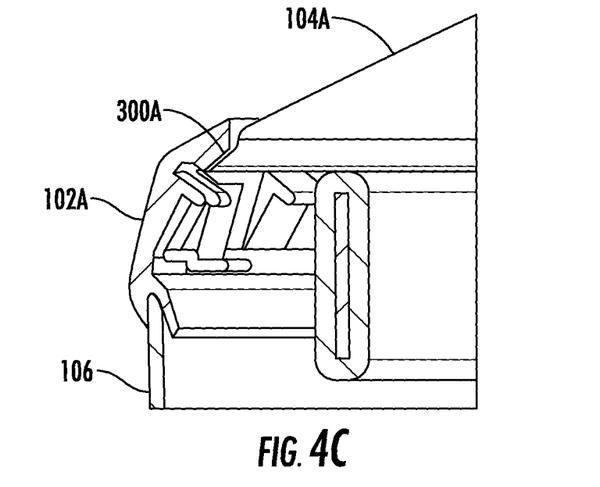
FIG. 4C shows a cross-sectional view of the face shield having a snap fit interface between an example protective element and an example opening of an example frame, according to an example embodiment.
Figure 4D:
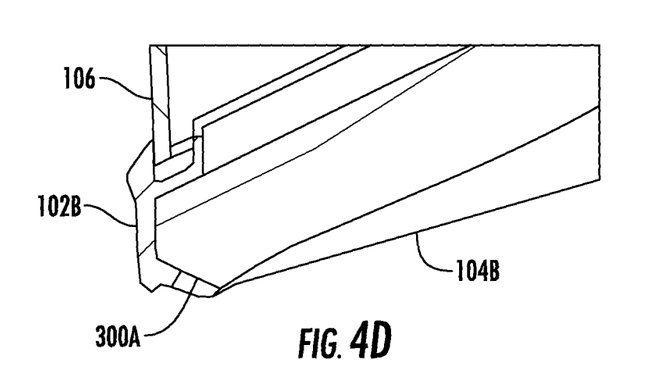
FIG. 4D shows a cross-sectional view of the face shield having a snap fit interface between an example protective element and an example opening of an example frame, according to an example embodiment.

With reference to FIGS. 4C and 4D, there is illustrated an interfacing between the continuous inner face seal edge $104_{Inner\ Edge}$ of the face seal 104, and the continuous inner frame edge $102_{Inner\ Edge}$ of the frame 102 of the protective face shield assembly 100. In some embodiments, the first affixing mechanism 300A may be used to provide an interface between the continuous inner face seal edge $104_{Inner\ Edge}$ of the face seal 104, and the continuous inner frame edge $102_{Inner\ Edge}$ of the frame 102 of the protective face shield assembly 100. One component of the first affixing mechanism 300A, such as the first fabric strip component 302, may be affixed towards the upper portion of the continuous inner frame edge $102_{Inner\ Edge}$ of the frame 102 along the complete periphery encompassing the front band structure 102A, the bottom band structure 102B, and the side band structures 102C and 102D. The tiny hooks 302A of the first fabric strip component 302 may receive the tiny loops 304A of the second fabric strip component 304 affixed on the continuous inner face seal edge $104_{Inner\ Edge}$ of the face seal 104. Upon applying some pressure, the tiny hooks 302A of the first fabric strip component 302 may get interlocked with the tiny loops 304A of the second fabric strip component 304, and the continuous inner face seal edge $104_{Inner\ Edge}$ of the face seal 104 is removably affixed to the continuous inner frame edge $102_{Inner\ Edge}$ of the frame 102. It may be noted that for brevity, only the side views of the front band structure 102A and the bottom band structure 102B are illustrated and described herein. However, the present disclosure may be contemplated to have the same interfacing all along the opening 108 of the frame 102, without any deviation from the scope of the disclosure.

Figure 5A:
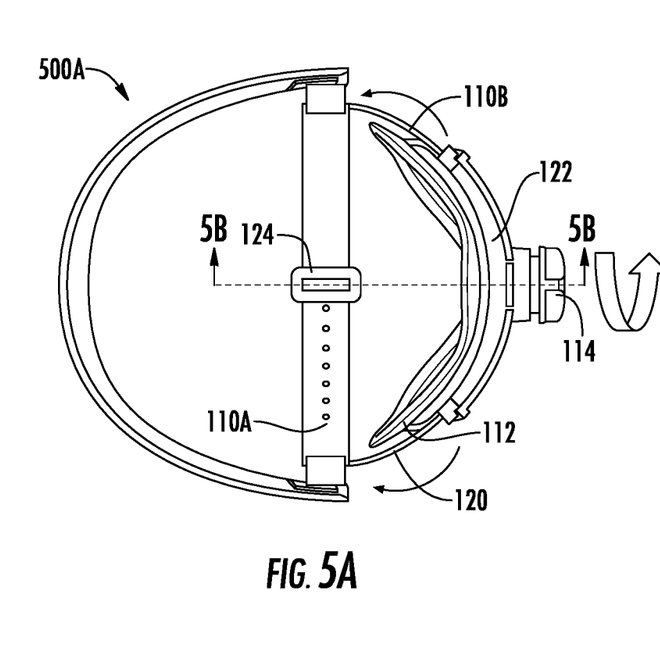
FIG. 5A illustrates a top view of an example adjustable back support member and an approach for using a fitting mechanism, according to an example embodiment.
Figure 5B:
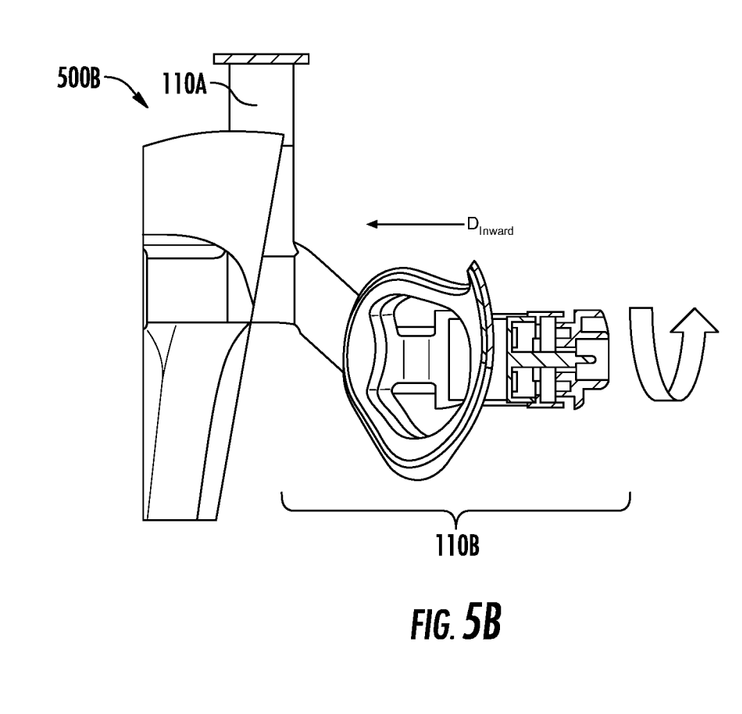
FIG. 5B illustrates a cross-sectional view of the fitting mechanism and adjustable back support member illustrated in FIG. 5A.

FIGS. 5A-5D illustrate fitting mechanisms provided by the adjustable back support member 110B, according to example embodiments. With reference to FIGS. 5A and 5B, there are shown, respectively, a top view 500A and a cross-sectional side view 500B of the adjustable back support member 110B. With reference to the top view 500A in FIG. 5A, the knob member 114 may be rotated along its pin axis in a clockwise direction. The bracket member 122 may house a ratchet module that may be configured to retract the slidable member 120 inwards towards the bracket member 122 when the knob member 114 is rotated along its pin axis in a clockwise direction. The retraction movement is depicted by arrow $D_{Inward}$ in the cross-sectional side view 500B. As the slidable member 120 retracts, the collective circumference of the front band structure 102A and the adjustable back support member 110B reduces, such that the protective face shield assembly 100 suitably fits the user.

Figure 5C:
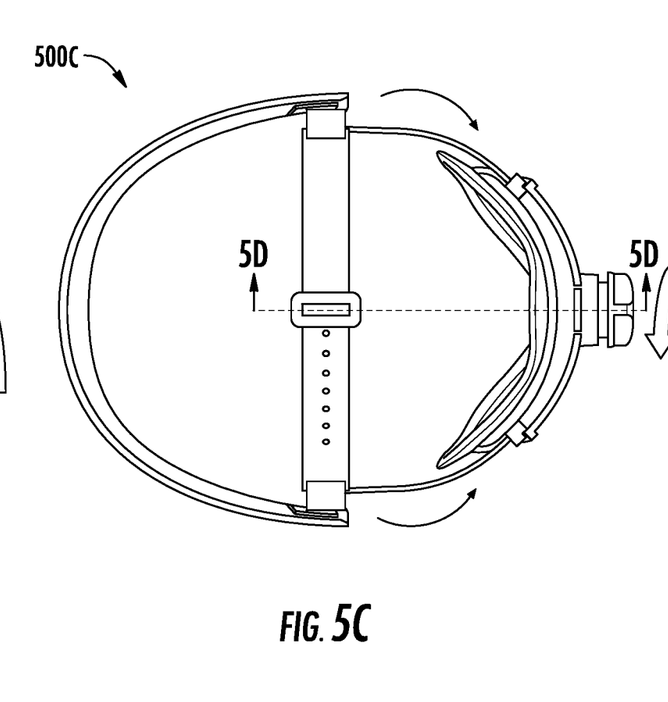
FIG. 5C illustrates a top view of an example adjustable back support member and an approach for using a fitting mechanism, according to another example embodiment.
Figure 5D:
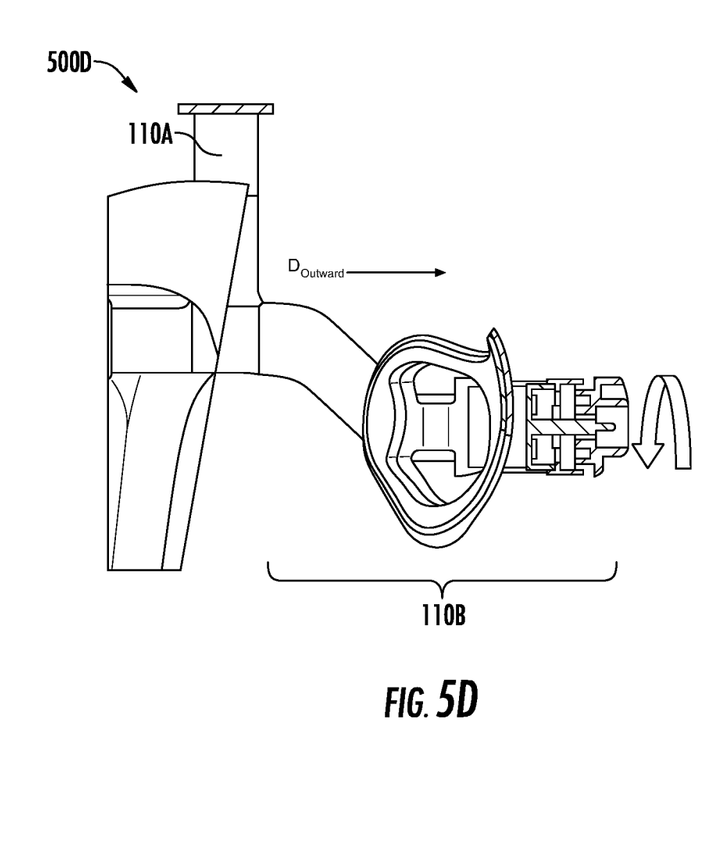
FIG. 5D illustrates a cross-sectional view of the fitting mechanism and adjustable back support member illustrated in FIG. 5C.

With reference to FIGS. 5C and 5D, there are shown, respectively, a top view 500C and a cross-sectional side view 500D of the adjustable back support member 110B. With reference to the side view 500D, the knob member 114 may be rotated along its pin axis in a counter-clockwise direction. The bracket member 122, housing the ratchet module, may be configured to extend the slidable member 120 outwards the bracket member 122 when the knob member 114 is rotated along its pin axis in a counter-clockwise direction. The extension movement is depicted by arrow $D_{Outward}$ in the cross-sectional side view 500D. As the slidable member 120 extends, the collective circumference of the front band structure 102A and the adjustable back support member 110B increases, such that the protective face shield assembly 100 suitably fits the user.

Also, it should be understood that the figures, which highlight the structure, methodology, functionality, and advantages of the present disclosure, are presented as examples only. The present disclosure is sufficiently flexible and configurable, such that it may be implemented in ways other than that shown in the accompanying figures.

Also, the section headings used herein are provided for consistency with the suggestions under 37 C.F.R. 1.77 or to otherwise provide organizational cues. These headings shall not limit or characterize the disclosure(s) set out in any claims that may issue from this disclosure. For instance, a description of a technology in the "Background" is not to be construed as an admission that certain technology is prior art to any disclosure(s) in this disclosure. Neither is the "Summary" to be considered as a limiting characterization of the disclosure(s) set forth in issued claims. Furthermore, any reference in this disclosure to "disclosure" in the singular should not be used to argue that there is only a single point of novelty in this disclosure. Multiple disclosures may be set forth according to the limitations of the multiple claims issuing from this disclosure, and such claims accordingly define the disclosure(s), and their equivalents, that are protected thereby. In all instances, the scope of the claims shall be considered on their own merits in light of this disclosure, but should not be constrained by the headings set forth herein.

Many modifications and other embodiments of the inventions set forth herein will come to mind to one skilled in the art to which these inventions pertain having the benefit of the teachings presented in the preceding descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above but is defined by the claims which follow, that scope including all equivalents of the subject matter of the claims. Every claim is incorporated as further disclosure into the specification, and the claims are embodiment(s) of the present disclosure(s). Furthermore, any advantages and features described above may relate to specific embodiments, but shall not limit the application of such issued claims to processes and structures accomplishing any or all of the above advantages or having any or all of the above features.

What is claimed is:

1. A protective face shield comprising:
   a protective element including an outer edge and an inner surface, wherein the inner surface of the protective element is a hydrophilic surface;
   a frame including a front band structure, a bottom band structure, and side band structures,
   wherein the front band structure, the bottom band structure, and the side band structures of the frame define a continuous inner frame edge and a continuous outer frame edge, and
   wherein the continuous outer frame edge defines an opening sized to fit the outer edge of the protective element; and
   a face seal having a top portion, a bottom portion, and side portions, wherein the top portion, the bottom portion and the side portions of the face seal are formed as a single continuous element and define a continuous inner face seal edge and a continuous outer face seal edge,
   wherein the continuous inner face seal edge is removably affixed against the continuous inner frame edge of the frame,
   wherein the continuous outer face seal edge encapsulates an elastic band that is configured to fit against at least a front half of a head and face portion of a user,
   wherein an interior air space of the face seal contains one or more layers of filter medium suitable for removing particulate matter from air that flows from an exterior air space and into the interior air space,
   wherein one of the frames or the face seal includes a battery-operated ventilator configured to regulate air flow from the interior air space to the exterior air space,
   wherein the continuous inner face seal edge is affixed against the continuous inner frame edge of the frame to prevent air leakage using a push-and-fit mechanism,
   wherein the push-and-fit mechanism comprises at least one groove component and at least one profile component, and
   wherein the at least one groove component is operably coupled to the at least one profile component.

2. The protective face shield according to claim 1, wherein a head suspension member is adapted to support the frame through an adjustable top support member and an adjustable back support member,
   wherein the adjustable top support member is configured to provide a top support to the frame, and
   wherein the adjustable back support member is configured to provide a back support to the frame.

3. The protective face shield according to claim 2, wherein the adjustable back support member comprises an additional support member adapted to provide additional support to the frame from a back portion of a head, and
   wherein fitting of the adjustable back support member is controlled by a knob member positioned at the adjustable back support member.

4. The protective face shield according to claim 1, wherein the continuous outer frame edge of the frame has a groove structure that receives the outer edge of the protective element and locks the protective element in the groove structure using a snap and fit mechanism.

5. The protective face shield according to claim 1, wherein an interface between the outer edge of the protective element and the continuous outer frame edge of the frame is air-tight to create an air path of maximum resistance for air flow, and wherein another interface between the continuous inner frame edge of the frame and the continuous outer face seal edge of the face seal is air-tight to create an air path of maximum resistance for air flow.

6. The protective face shield according to claim 1, wherein the one or more layers of the filter medium of the face seal creates an air path of least resistance for air flow.

7. The protective face shield according to claim 1, wherein the exterior air space corresponds to an air space outside the protective face shield, wherein the interior air space corresponds to air space inside the protective face shield.

8. The protective face shield according to claim 1, wherein the continuous inner face seal edge is affixed against the continuous inner frame edge of the frame to prevent air leakage using a double-sided adhesive tape.

9. The protective face shield according to claim 1, wherein the continuous inner face seal edge is affixed against the continuous inner frame edge of the frame to prevent air leakage using a hook and loop fastener.

10. The protective face shield according to claim 1, wherein the face seal containing the one or more layers of the filter medium has pleats to increase an effective surface area of the face seal.

11. The protective face shield according to claim 1, wherein at least one of the one or more layers of the filter medium comprises filter membranes made from nanofibers.

12. A protective face shield assembly comprising:
a protective element including an outer edge;
a frame including a semi-circular front band structure affixed with a head support member and having end portions, a curved bottom band structure, and two side band structures opposite and parallel to each other with chamfered lower end portions,
wherein the side band structures connect the opposite end portions, respectively, of the semi-circular front band structure with the curved bottom band structure to form a unified structure of the frame,
wherein the semi-circular front band structure, the curved bottom band structure, and the side band structures of the frame define a continuous inner frame edge and a continuous outer frame edge, and
wherein the continuous outer frame edge defines an opening sized to fit the outer edge of the protective element using a snap and fit mechanism;
a face seal having a top portion, a bottom portion, and side portions, wherein the top portion, the bottom portion and the side portions of the face seal are formed as a single continuous element and define a continuous inner face seal edge and a continuous outer face seal edge,
wherein the continuous inner face seal edge is affixed against the continuous inner frame edge of the frame to prevent air leakage using a hook and loop mechanism,
wherein the continuous outer face seal edge encapsulates an elastic band that is configured to fit against at least a front half of head and face portion of a user, and
wherein an interior air space of the face seal contains one or more layers of filter medium suitable for removing particulate matter from an air that flows from an exterior air space and into the interior air space, wherein the filter medium has pleats to increase an effective surface area of the face seal; and
a head suspension member adapted to support the frame through an adjustable top support member and an adjustable back support member,
wherein the adjustable top support member is designed to be substantially in an orthogonal plane with respect to the semi-circular front band structure,
wherein two ends of the adjustable top support member are engaged with opposite ends of the semi-circular front band structure to provide a top support to the frame,
wherein the adjustable back support member orthogonally extends out from the adjustable top support member and chamfers downward towards a back portion of the frame,
wherein the adjustable back support member comprises an additional support member adapted to provide additional support to the frame from a back portion of a head of the user,
wherein fitting of the adjustable back support member is controlled by a knob member positioned at the adjustable back support member,
wherein one of the frames or the face seal includes a battery-operated ventilator configured to regulate air flow from the interior air space to the exterior air space,
wherein the continuous inner face seal edge is affixed against the continuous inner frame edge of the frame to prevent air leakage using a push-and-fit mechanism,
wherein the push-and-fit mechanism comprises at least one groove component and at least one profile component, and
wherein the at least one groove component is operably coupled to the at least one profile component.

13. The protective face shield assembly according to claim 12, wherein the continuous outer frame edge of the frame has a groove structure that receives the outer edge of the protective element and locks the protective element in the groove structure using the snap and fit mechanism.

14. The protective face shield assembly according to claim 12, wherein the protective element is permanently fixed in the continuous outer frame edge of the frame.

15. The protective face shield assembly according to claim 12, wherein the protective element is a part of the unified structure of the frame.

16. The protective face shield assembly according to claim 12, wherein an interface between the outer edge of the protective element and the continuous s outer frame edge of the frame is air-tight to create an air path of maximum resistance for air flow, and
wherein another interface between the continuous inner frame edge of the frame and the continuous outer face seal edge of the face seal is air-tight to create an air path of maximum resistance for air flow.

17. The protective face shield assembly according to claim 12, wherein the one or more layers of the filter medium of the face seal creates an air path of least resistance for air flow.

* * * * *